United States Patent [19]
Rasmusson et al.

[11] Patent Number: 5,693,810
[45] Date of Patent: Dec. 2, 1997

[54] 17 β-CARBOXANILIDES OF 4-AZA-5α-ANDROSTAN-3-ONES AS 5α-REDUCTASE INHIBITORS

[75] Inventors: Gary H. Rasmusson, Watchung; Raman K. Bakshi, Edison; Gool F. Patel, Califon, all of N.J.

[73] Assignee: Merck & Co., Inc., Rahway, N.J.

[21] Appl. No.: 406,898

[22] PCT Filed: Oct. 6, 1993

[86] PCT No.: PCT/US93/09585

§ 371 Date: Mar. 21, 1995

§ 102(e) Date: Mar. 21, 1995

[87] PCT Pub. No.: WO94/07861

PCT Pub. Date: Apr. 14, 1994

Related U.S. Application Data

[63] Continuation-in-part of Ser. No. 957,231, Oct. 6, 1992, abandoned.

[51] Int. Cl.$^6$ ................................................ A61K 31/58
[52] U.S. Cl. ................................................ 546/77; 514/284
[58] Field of Search ................................... 546/77; 514/284

[56] References Cited

U.S. PATENT DOCUMENTS

| | | | |
|---|---|---|---|
| 4,377,584 | 3/1983 | Rasmusson et al. | 546/77 |
| 4,760,071 | 7/1988 | Rasmusson et al. | 546/77 |
| 5,116,983 | 5/1992 | Bhattacarrya et al. | 546/77 |
| 5,302,621 | 4/1991 | Kojima | 546/77 |
| 5,304,562 | 4/1994 | Biollaz | 514/284 |
| 5,565,467 | 10/1996 | Batchelor et al. | 546/77 |

FOREIGN PATENT DOCUMENTS

| | | |
|---|---|---|
| 0484094 | 5/1992 | European Pat. Off. |
| 93 23420 | 11/1993 | WIPO |
| 95-12398 | 5/1995 | WIPO |

OTHER PUBLICATIONS

Roberts et al. "Basic Principles of Organic Chemistry" W.A. Benjamin, N.Y., 1964 p. 681.
Stinson, Chem & Eng News Jun. 29, 1992 pp 7–8.
Helliker, Wall St. Jour. Jun. 7 1991 pp A1, A7 (1991).
Burger, Ed. "Medicinal Chemistry"2d. Ed. Interscience, NY, 1960 p. 42.
Kojima, Chem Abstr. vol 117 entry 49007 –(May 1992).
Bakshi et al., J. Med. Chem., vol. 38, No. 17 (Aug. 18, 1995), pp. 3189–3192.
The Daily (Tuesday, May 7, 1996), "New Data on Proscar, Abbott's Hytrin Show Conflicting Results".
Winslow Wall Street Journal (Tuesday, May 7, 1996), "Study Finds Abbott's Prostate Drug is Much More Effective than Merck's", p. B4.
US News & World Report, May 20, 1996, "Zapping a problem prostate".

Primary Examiner—Donald G. Daus
Attorney, Agent, or Firm—Catherine D. Fitch; Melvin Winokur

[57] ABSTRACT

Described are new 17β-carboxanilides of 4-aza-5α-androstan-3-ones and related compounds of structural formula I:

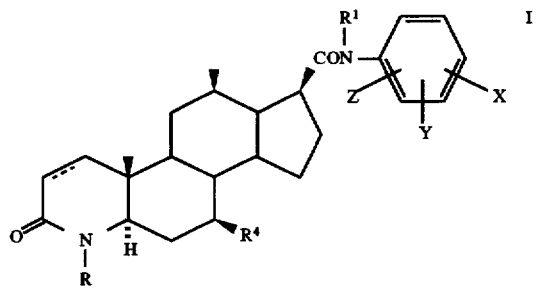

and the use of such compounds as 5α-reductase inhibitors for treatment of benign prostatic hyperplasia acne, seborrhea, female hirsutism, prostatitis, and prostatic carcinoma and other hyperandrogenetic related disorders.

3 Claims, No Drawings

17 β-CARBOXANILIDES OF 4-AZA-5α-ANDROSTAN-3-ONES AS 5α-REDUCTASE INHIBITORS

CROSS REFERENCE TO RELATED APPLICATIONS

This application is national phase application under 35 U.S.C §371 of PCT application Ser. No. PCT/US93/09585, filed Oct. 6, 1993, published as WO94/07861 Apr. 14, 1994, which, in turn is a continuation in part of application Ser. No. 07/957,231 filed Oct. 6, 1992, now abandoned.

BACKGROUND OF THE INVENTION

The present invention is directed to new 17β-carboxanilides of 4-aza-5α-androstan-3-ones and related compounds and the use of such compounds as 5α-reductase inhibitors.

DESCRIPTION OF THE PRIOR ART

The art reveals that certain undesirable physiological manifestations, such as acne vulgaris, seborrhea, female hirsutism, male pattern baldness and benign prostatic hyperplasia, are the result of hyperandrogenetic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3-trifluoromethyl-isobutyranilide. See Neri, et at., Endo., Vol. 91, No. 2 (1972). However, these products, though devoid of hormonal effects, compete with all natural androgens for receptor sites, and hence have a tendency to feminize a male host or the male fetus of a female host and/or initiate feed-back effects which would cause hyperstimulation of the testes.

It is now known in the art that the principal mediator of androgenic activity in some target organs, e.g. the prostate, is 5α-dihydrotestosterone, and that it is formed locally in the target organ by the action of testosterone-5α-reductase. It is also known that inhibitors of testosterone-5α-reductase will serve to prevent or lessen symptoms of hyperandrogenetic stimulation.

For example, a number of 4-aza steroid compounds are known which are 5α-reductase inhibitors. See the following Merck & Co., Inc. patents, U.S. Pat. Nos. 4,377,584, 4,220, 775, 4,859,681, 4,760,071 and the articles J. Med. Chem. 27, p. 1690–1701 (1984) and J. Med. Chem. 29, 2998–2315 (1986) of Rasmusson, et al., and U.S. Pat. No. 4,845,104 to Carlin, et al., and U.S. Pat. No. 4,732,897 to Cainelli, et at., and EP Publication No. 0 484 094 to Sankyo, which describe 4-aza-17β-substituted-5 α-androstan-3-ones said to be useful in the treatment of DHT-related hyperandrogenic conditions.

However, none of the above references specifically describe the compounds of the instant invention, which are selective and potent inhibitors of 5α-reductase in humans, as well as animals, i.e. dogs, which are exceptionally active.

SUMMARY OF THE INVENTION

The present invention discloses novel anilide derivatives of 17β-carboxy-4-aza-5α-androstan-3-ones which are useful for inhibiting the 5α-reductase enzyme in prostatic tissue and isozymes thereof. They are also particularly effective in selectively inhibiting mammalian 5α-reductase for the treatment of benign prostatic hyperplasia in humans and dogs, acne, female hirsutism, androgenic alopecia, i.e., male pattern baldness and treatment of prostatic carcinoma.

In accordance with the present invention there is provided novel anilides of 17β-carboxy-4-aza-5α-androstan-3-one and related compounds of the formula:

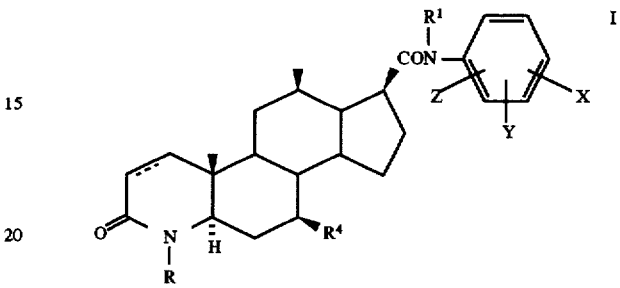

wherein:

R is H, $CH_3$, or $C_2H_5$;

$R_1$ is H, $C_1$–$C_{10}$ alkyl, or phenyl; and

X, Y and Z independently represent —H; —OH; —$NH_2$; SH; —$SC_1$-$C_4$alkyl;

—$CO_2H$; —CN; —$C_2$–$C_{10}$ acyl; —$C_7$–$C_{15}$ aroyl; straight or branched chain alkyl having 3, 4, 5, 6, 7, or 8 carbon atoms; —$C_3$–$C_8$ cycloalkyl; -$C_6$–$C_{14}$ aryl; heteroaryl; heteroaroyl; —$C_7$–$C_{10}$ aralkyl; —$CONR^2R^3$ where $R^2$ and $R^3$ independently are H, $C_{1-8}$ alkyl, $C_{3-8}$ cycloalkyl, $C_6$–$C_{14}$ aryl, or $R^2$ and $R^3$ together with the nitrogen to which they are attached form a 5–7 membered saturated heterocyclic ring containing 1–2 nitrogen atoms, and 0–1 oxygen atoms;
—$NHCOR^2$;
—$OCOR^2$;
—$NR^2(CO)R^3$;
—$NR^2(CO)NHR^3$;
—$NHSO_2R^2$;
—$OR^2$;
—$NR^2R^3$;
—$CO_2R^2$;

provided that X, Y, and Z cannot simultaneously be —H when $R^1$ is —H or $C_1$–$C_{10}$ alkyl, and provided further that X, Y, and Z cannot simultaneously be —H when $R^1$ is phenyl and $R^4$ is —H or methyl; and wherein the aryl, aroyl, heteroaryl, and heteroaroyl substituents can be unsubstituted or substituted by 1-3 substituents as defined above for X, Y and Z;

$R^4$ can be:

1) oxo;
2) alpha-hydrogen and beta-hydrogen or a beta-substituent selected from: $C_1$–$C_4$ alkyl; $C_2$–$C_4$ alkenyl; —$CH_2COOH$; hydroxy; carboxy; —$COOC_1$–$C_4$ alkyl esters; —$OCONR^5R^6$, wherein $R^5$ and $R^6$ are independently H, $C_1$–$C_4$ alkyl, phenyl, benzyl, or $R_5$ and $R_6$ together with the nitrogen to which they are attached can form a 5–6 membered saturated heterocyclic ring, optionally containing one other heteroatom; —$OC_1$–$C_4$ alkyl; —$OC_3$–$C_6$ cycloalkyl; —$OCOCH_3$; halo; hydroxy $C_1$–$C_2$ alkyl; halo $C_1$–$C_2$ alkyl; trifluoromethyl; and $C_3$–$C_6$ cycloalkyl;

3) =CH—R' where R' is H, or $C_1$-$C_4$ alkyl;
4) spiro:

where R' is H, or $C_1$-$C_4$ alkyl; and wherein the dashed line can represent a double bond when present; and pharmaceutically acceptable salts and esters thereof.

Also disclosed are processes for their preparation, pharmaceutical formulations comprising the novel compounds as active ingredients and methods of inhibiting 5α-reductase in diseases which occur under hyperandrogenetic conditions, e.g., benign prostatic hyperplasia.

DETAILED DESCRIPTION OF THE INVENTION AND PREFERRED EMBODIMENTS

The structure I above encompasses all the 5α-reductase inhibitor compounds of this invention.

The dashed line can independently be a double bond and, when present, the compound is a delta-1-ene.

The aryl ring of the anilide can be unsubstituted or substituted with one or more of the following substituents indicated by X, Y and Z, providing the substitution leads to a chemically stable, but biologically active 5α-reductase inhibitor.

By the term "$C_1$-$C_4$ alkyl" is meant linear or branched alkyl; e.g. methyl, ethyl, isopropyl, propyl, n-butyl, isobutyl, sec-butyl and the like.

By the term "hydroxy $C_1$-$C_2$ alkyl" is meant monohydroxy $C_1$-$C_2$ alkyl including: hydroxymethyl, 1-hydroxyethyl, 2-hydroxyethyl, and the like.

By the term "halo $C_1$-$C_2$ alkyl" is meant mono halogenated $C_1$-$C_2$ alkyl including: fluoromethyl, chloromethyl, 1-fluoroethyl, 2-fluoroethyl, 1-chloroethyl, 2-chloroethyl, and the like.

By the term "$OC_1$-$C_4$ alkyl" as used herein is meant to include methoxy, ethoxy, propoxy, isopropoxy, n-butoxy, isobutoxy, sec-butoxy, t-butoxy, and the like.

By the term "$OC_3$-$C_6$ cycloalkyl" as used herein is meant to include: cyclopropyloxy, cyclobutyloxy, cyclopentyloxy, cyclohexyloxy, and the like.

$C_2$-$C_4$ alkenyl includes ethenyl, allyl, 1- and 2-butenyl and the like.

$C_3$-$C_6$ cycloalkyl includes cyclopropyl, cyclobutyl, cyclopentyl, cyclohexyl, and the like.

"Halo" includes fluoro, chloro, bromo and preferred is fluoro, chloro.

$R_5$ and $R_6$ can also be connected to form a 5–6 membered heterocyclic radical, being fully saturated, containing 1–2 nitrogen atoms and 0–1 oxygen atoms, e.g., piperidino, pyrrolidino, morpholino, and the like.

The phenyl and benzyl groups in $R_5$ and $R^6$ can be unsubstituted or substituted with one or more of the following substituents providing the substitution leads to a chemically stable, but biologically active 5-alpha reductase inhibitor:

The ring substituents include:
$C_1$-$C_4$ straight or branched alkyl;
$C_1$-$C_5$ alkoxy; and
halo; all as defined above.

Representative examples of $R^4$ are where the α-substituent (dashed lines) is hydrogen and the beta substituent (wedge) is e.g. methyl, ethyl, propyl, allyl, carboxymethyl, hydroxy, methoxy, ethoxy, cyclopropyloxy, cyclopentyloxy, acetoxy, fluoro, chloro, bromo, trifluoromethyl, trichloromethyl, fluoromethyl, chloromethyl, carboxy, N,N-dimethylcarbamate, hydroxymethyl, methoxymethyl, and the like.

Representative examples where $R^4$ is an alkenyl substituent, =CH—R', includes, e.g. =$CH_2$, =CH—$CH_3$, =CH—$CH_2CH_3$, and the like.

Representative examples where $R^4$ is the spiro substituent:

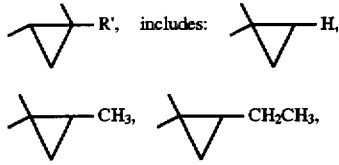

stereoisomers thereof and the like.

By the term "$C_1$-$C_{10}$ alkyl" is meant linear or branched alkyl hydrocarbon; e.g. methyl, ethyl, isopropyl, propyl, n-butyl, isobutyl, sec-butyl, t-butyl, n-pentyl, n-hexyl, isohexyl, n-octyl, iso-octyl, t-octyl, n-decyl, and the like.

By the term "$C_1$-$C_8$ alkyl" is meant a saturated straight or branched chain hydrocarbon radical containing 1–8 carbons including those described above.

By the term "$C_3$-$C_8$ cycloalkyl" is meant e.g., cyclopropyl, cyclobutyl, cyclopentyl, cyclohexyl, 1-methylcyclobutyl, cyclopentyl, cyclohexyl, 1-methyl-cyclohexyl, 2-methylcyclohexyl, 2-ethylcyclohexyl, and the like;

By the term "$C_2$-$C_{10}$ acyl" is meant $C_1$-$C_9$ alkylcarbonyl, including acetyl, n-propionyl, iso-butyryl, n-decanoyl, and the like.

By the term "$C_7$-$C_{15}$ aroyl" is meant arylcarbonyl, including benzoyl, naphthoyl and anthranoyl.

By the term "$C_6$-$C_{14}$ aryl" is meant a mono or polycyclic carbocyclic aromatic radical, including phenyl, naphthyl, anthranyl, and the like.

By the term "$C_7$-$C_{10}$ aralkyl" is meant a phenyl substituted $C_1$-$C_3$ alkyl chain including benzyl, 1-phenylethyl, 2-phenylethyl, 3-phenylpropyl and the like.

The anilide phenyl ring substituents in addition to those above include:

"heteroaryl" being a 5–7 membered aromatic ring containing 0–4 nitrogen atoms and 0–1 oxygen or 0–1 sulfur atoms, which can be 1,2-fused with a benzo ring or another heteroaryl ring as defined above; included in this definition are the following:

pyridyl, furyl, pyrryl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl, and benzoxazolyl, and the like, which can be further substituted by 1–3 of X, Y and Z as defined herein;

"heteroaroyl" including the above described heteroaryl rings attached to a —C(=O)— group including:

pyridoyl, furoyl, pyrroyl, thienoyl, isothiazoloyl, imidazoloyl, benzimidazoloyl, tetrazoloyl, pyrazinoyl, pyrimidoyl, quinoloyl, isoquinoloyl, benzofuroyl, isobenzofuroyl, benzothienoyl, pyrazoloyl, indoloyl, isoindoloyl, purinoyl, carbazoloyl, isoxazoloyl, thiazoloyl, oxazoloyl, benzthiazoloyl, benzoxazoloyl, and the like, which can be further substituted by 1–3 of X, Y and Z as defined herein;

—$CONR^2R^3$, where $R^2$ and $R^3$ independently are H, $C_1$-$C_8$ alkyl, $C_3$-$C_8$ cycloalkyl, $C_6$-$C_{14}$ aryl, all as defined above; and together they can form a 5–7 membered saturated heterocyclic ring containing 1–2 nitrogen atoms, and 0–1 oxygen atoms, e.g. piperidino, piperazino, pyrrolidino, morpholino;

—NHCOR$^2$, including acetylamino, isobutyrylamino, n-octanoylamino, 2-adamantanoylamino, 2-pyridylcarbonyl-amino, pivaloylamino, benzoylamino, and the like;

—OCOR$^2$, including acetoxy, propionoyloxy, cyclopropanecarboxy, 2-adamantanecarboxy, t-butanecarboxy, 2-pyridocarboxy, and the like;

—NR$^2$(CO)R$^3$, including formylamino, acetylamino, butyrylamino, benzamido, 2-adamantanecarboxamido, benzoylamino, and the like;

—NR$^2$(CO)NHR$^3$, including ureido, N1-benzylureido, N1-ethylureido, N2-methylureido, and the like;

—NHSO$_2$R$^2$, including phenylsulfonamido, methylsulfonamido, benzylsulfonamido, toluenesulfonamido, trifluoromethanesulfonamido, and the like;

—OR$^2$, including methoxy, ethoxy, phenoxy, cyclopropoxy, t-butoxy, and the like;

—NR$^2$R$^3$, including methylamino, ethylamino, dimethylamino, diethylamino, diisopropylamino, pyrrolidino, morpholino, and the like;

—CO$^2$R$^2$, including methoxycarbonyl, ethoxycarbonyl, t-butoxycarbonyl, benzoxycarbonyl, 2-adamantoxycarbonyl, and the like.

In addition, C$_7$–C$_{15}$ aroyl and C$_6$–C$_{14}$ aryl can be substituted by 1–3 X, Y or Z substituents as defined herein.

Preferably the anilide ring is monosubstituted, with one of the above-described substituents where at least two of X, Y or Z are H, or where the anilide phenyl ring is completely unsubstituted.

Any substitutions which result in the formation of compounds containing quaternary nitrogen atoms are not intended to be within the scope of the present invention.

Representative compounds of the present invention include the following:

N-(4-hydroxyphenyl)-3-oxo-4-aza-5α-androst-1-ene-17β-carboxamide, mp. 325° C.(d);

N-(3-hydroxyphenyl)-3-oxo-4-aza-5α-androst-1-ene-17β-carboxamide, mp. 289°–291° C.;

N-(2-hydroxyphenyl)-3-oxo-4-aza-5α-androst-1-ene-17β-carboxamide, mp. 297°–299° C.;

N-phenyl-3-oxo-4-aza-5α-androst-1-ene-17β-carboxamide, mp. 293°–295° C.;

N-(4-aminophenyl)-3-oxo-4-aza-5α-androst-1-ene-17β-carboxamide, mp. 277°–279° C.;

N-(3-aminophenyl)-3-oxo-4-aza-5α-androst-1-ene-17β-carboxamide, mp. 227°–228° C.;

N-(2-aminophenyl)-3-oxo-4-aza-5α-androst-1-ene-17β-carboxamide, mp. 274°–276° C.;

N-phenyl-3-oxo-4-methyl-4-aza-5α-androst-1-en-17β-carboxamide,

N-phenyl-3-oxo-4-aza-5α-androstane-17β-carboxamide, mp.285°–287° C.;

N-phenyl-3-oxo-4-aza-5α-androst-1-ene-17β-carboxamide,

N-phenyl-3-oxo-4-methyl-4-aza-5α-androstane-17β-carboxamide, mp. 281°–283° C.;

N-phenyl-3-oxo-7β-methyl-4-aza-5α-androstane-17β-carboxamide,

N-phenyl-3-oxo-4,7β-dimethyl-4-aza-5α-androstane-17β-carboxamide,

N-(4-carbomethoxy)phenyl-3-oxo-4-aza-5α-androstane-17β-carboxamide, mp. 287°–289° C.;

N-(4-carbomethoxy)phenyl-3-oxo-4-aza-5α-androst-1-ene-17β-carboxamide, mp. 265°–267° C.;

N-(4-carboxyphenyl)-3-oxo-4-aza-5α-androstane-17β-carboxamide, mp. 355°–357° C.;

N-(4-carbomethoxy)phenyl-N-methyl-3-oxo-4-methyl-4-aza-5α-androstane-17β-carboxamide, mp. 149°–150° C.;

N-(4-carbomethoxy)phenyl-N-methyl-3-oxo-4-methyl-4-aza-5α-androst-1-ene-17β-carboxamide, mp. 96°–98°;

N-(2-carbomethoxy)phenyl-3-oxo-4-aza-5α-androstane-17β-carboxamide, mp. 128°–129° C.;

N-(2-methoxycarboxy)phenyl-3-oxo-4-aza-5α-androst-1-ene-17β-carboxamide, mp. 115°–116° C.;

N-(4-aminophenyl)-3-oxo-4-aza-5α-androstane-17β-carboxamide, mp. 295° C.;

N-(4-aminophenyl)-3-oxo-4-methyl-4-aza-5α-androstane-17β-carboxamide, mp. 304°–307° C.(d);

N-4-acetamidophenyl-N-acetyl-3-oxo-4-methyl-4-aza-5α-androstane-17β-carboxamide, mp. 335°–336° C.;

N-4-acetamidophenyl-3-oxo-4-methyl-4-aza-5α-androstane-17β-carboxamide, mp. 144°–147° C.;

N-4-acetamidophenyl-3-oxo-4-aza-5α-androstane-17β-carboxamide mp. 335°–336° C.;

N-4-pivalamidophenyl-3-oxo-4-methyl-4-aza-5α-androstane-17β-carboxamide, mp. 296°–298° C.;

N-4-isobutyramidophenyl-3-oxo-4-methyl-4-aza-5α-androstane-17β-carboxamide, mp. 260°–261° C., and also including the corresponding compounds wherein the 4-hydrogen substituent is replaced by a methyl or an ethyl radical, and where a delta-one double bond is present.

Also included within the scope of this invention are pharmaceutically acceptable salts, i.e. hydrochloride, hydrobromide, acetate, pamoate, and the like, which can be used as the dosage form for modifying solubility or hydrolysis characteristics or for use as sustained release or prodrug formulations.

Accordingly, the present invention is particularly concerned with providing a method of treating the hyperandrogenic conditions of acne vulgaris, seborrhea, female hirsutism as well as benign prostatic hyperplasia, prostatitis, and prostatic carcinoma by oral or parenteral administration of the novel compounds of the present invention.

The present invention is thus also concerned with providing suitable topical, oral and parenteral pharmaceutical formulations for use in the novel methods of treatment of the present invention.

The compositions containing the compounds of the present invention as the active ingredient for use in the treatment of benign prostatic hypertrophy can be administered in a wide variety of therapeutic dosage forms in conventional vehicles for systemic administration, as, for example, by oral administration in the form of tablets, capsules, solutions, or suspensions, or by intravenous or intramuscular injection or by subdermal implantation, i.e., in the male dog. The dosage of the products for an adult human/per day or for a male dog can be varied over a wide range varying from 0.5 to 1,000 mg. The compositions are preferably provided in the form of scored tablets containing 0.5, 1.0, 2.5, 5.0, 10.0, 15.0, 25.0,and 50.0 milligrams of the active ingredient for the symptomatic adjustment of the dosage to the patient to be treated. An effective amount of the drug is ordinarily supplied at a dosage level of from about 0.002 mg. to about 50 mg./kg. of body weight per day. Preferably the range is from about 0.01 mg. to 7 mg./kgs. of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calciuim phosphate, lactose, corstarch or magnesium stearate. The liquid forms in suitably flavored suspending or dispersing agents such as the synthetic and natural gums, for example, tragacanth, acacia, methylcellulose and the like. Other dispersing agents which can be employed include glycerin and the like. For parenteral administration, suitably prepared implants or sterile suspensions and solutions are desired. Isotonic preparations which generally contain suitable preservative are employed when intravenous administration is desired.

For the treatment of acne vulgaris, seborrhea, female hirsutism, the compounds of the present invention can be administered in the formula of pharmaceutical composition comprising the active compound in combination with a pharmacologically acceptable carrier adapted for topical administration. Parenteral administration is also applicable. These topical pharmaceutical compositions can be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

A method for preparing the novel anilide derivatives of 17β-carboxy-3-oxo-4-azasteroids of the present invention, already described above in general terms, may be further illustrated by the following examples and synthetic procedure.

A synthetic procedure for these anilides is:

Preparation of Intermediates

A. S-2'-pyridyl-3-oxo-4-aza-4-methyl-5α-androstane-17β-thiocarboxylate

To a solution of 3-oxo-4-aza-4-methyl-5α-androstane-17β-carboxylic acid (7.0 g, 21 mmol) in toluene (300 ml) was added aldrithiol (14.7 g, 66.7 mmol) and triphenylphosphine (16.49 g, 62.8 mmol). After stirring the reaction mixture overnight at room temperature, the reaction mixture was concentrated under vaccum and purified by column chromatography over silica gel using 10% acetone/methylene chloride as eluant to give 6.0 g of pure product.

B. S-2'-pyridyl-3-oxo-4-aza-5α-androst-1-ene-17β-thiocarboxylate

To a solution of 3-oxo-4-aza-5α-androst-1-ene-17β-carboxylic acid (10.0 g, 31.5 mmol) in toluene (60 ml) was added aldrithiol (14 g, 63.5 mmol) and triphenylphosphine (316 g, 61 mmol). After stirring the reaction mixture for overnight at room temperature, the product precipitated out of solution and was filtered (8.4 g).

C. S-2'-pyridyl-3-oxo-4-aza-5α-androstane-17β-thiocarboxylate

To a solution of 3-oxo-4-aza-5α-androstane-17β-carboxylic acid (20.0 g, 62.7 mmol) in toluene (120 ml) was added aldrithiol (28 g, 127 mmol) and triphenylphosphine (32 g, 122 mmol). After stirring the reaction mixture for overnight at room temperature, the product precipitated out of solution and was filtered (20 g), Mp 247°–249° C.

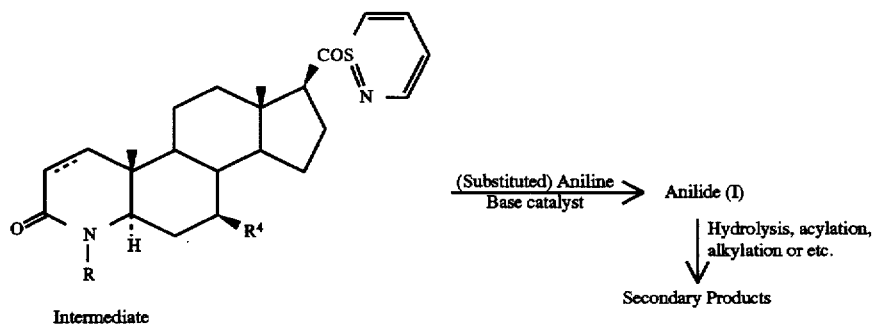

Intermediate

As seen in the above diagram, the 2-thiopyridyl intermediate (A, B or C) is reacted with an aniline, or substituted aniline, at room or elevated temperature, e.g. 25°–150° C., in the presence of a basic catalyst, e.g. an excess of the starting aniline, for a sufficient time, e.g. 6–24 hours, to form the desired anilide (see Examples 1–3). Conventional workup procedures are utilized to isolate and purify the new anilide.

Further, the new anilide can be subjected to a secondary reaction to yield another new anilide. For example see Examples 4–6. In Example 4, the carboxamido nitrogen is further methylated to form the N-methyl analog. In Example 5, the 4-amino anilide is acylated to yield the 4-isobutyloxyamino-phenyl analog. In Example 6, the 4-carbomethoxy anilide is saponified to the 4-carboxy analog. Thus, by starting with a substituted anilide, containing a functional group X, Y, Z, which can be further modified by a subsequent synthetic reaction, further new anilides can be obtained.

The following are preparations of intermediates useful in the invention and examples of compounds of the invention, which should not be construed to be limits on the scope or spirit of the instant invention.

EXAMPLE 1

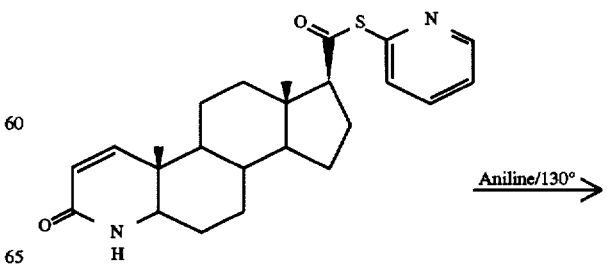

9
-continued

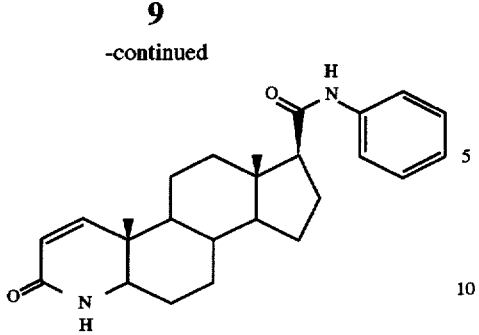

N-phenyl-3-oxo-4-aza-5α-androst-1-ene-17β-carboxamide

S-2'-pyridyl-3-oxo-4-aza-5α-androst-1-ene-17β-thiocarboxylate (205 mg, 0.5 mmol) was dissolved in aniline (1 ml) and solution heated at 130° for overnight. The reaction mixture was cooled and purified by preperative silica gel tlc (30% acetone/methylene chloride) to give pure titled product which was recrystallized from acetonitrile. Mp 293°–295° C. Mass spec. (MS) M$^+$ calculated 392.55; observed 393 (m+1). Anal. calcd for $C_{25}H_{32}N_2O_2$, C 76.49; H 8.21; N 7.14; Found C 76.59; H 8.26, N 7.13

EXAMPLE 2

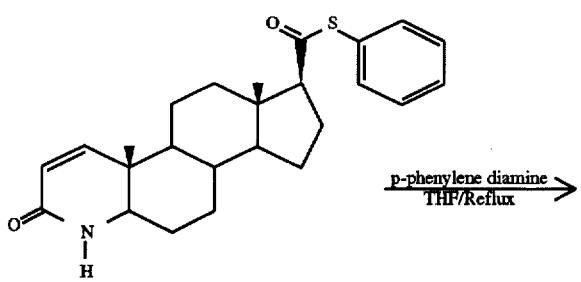

N-4-aminophenyl-3-oxo-4-aza-5α-androst-1-ene-17β-carboxamide

S-2'-pyridyl-3-oxo-4-aza-5α-androst-1-ene-17β-thiocarboxylate (200 mg) was dissolved in THF (25 ml) and to this p-phenylene diamine (200 mg) was added. After stirring the reaction mixture at reflux temperature for 6 hrs, the reaction mixture was cooled to room temperature and left for overnight. Reaction mixture was concentrated and purified by prep. silica gel tlc. Titled product (140 mg) was recrystallized from hot methanol, Mp 259°–262° C. Mass spec. (MS) M$^+$ calculated 407.56; observed 408 (m+1). Anal. calcd for $C_{25}H_{33}N_3O_2 \cdot 0.3\ H_2O$, C 72.71; H 8.20; N 10.18; Found C 72.89; H 8.01, N 10.27.

10
EXAMPLE 3

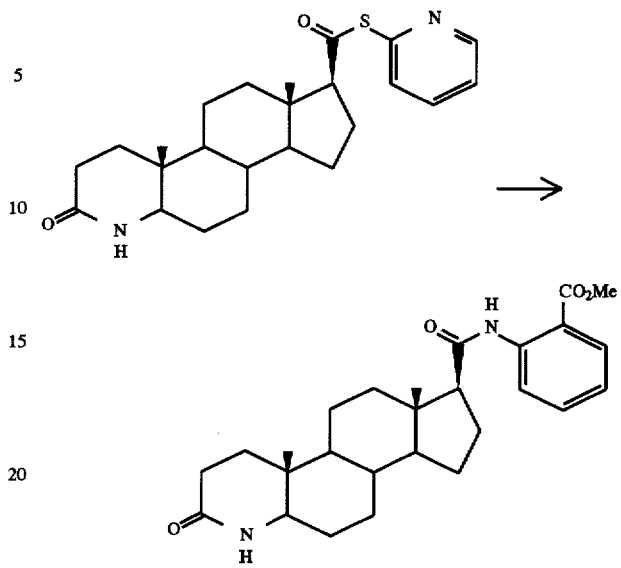

N-2-carbomethoxyphenyl-3-oxo-4-aza-5α-androstane-17β-carboxamide

S-2'-pyridyl-3-oxo-4-aza-5β-androstane-17β-thiocarboxylate (207 mg, 0.5 mmol) was dissolved in toluene (4 ml) and to this 2-methyl anthranilate (199.5 mg, 1.32 mmol) and silver trifluoromethanesulfonate (129 mg, 0.5 mmol) were added. After stirring the reaction mixture at room temperature for 2 days, the reaction mixture was concentrated, partitioned between methylene chloride and water, methylene chloride layer was washed with 5% aq. $NH_4OH$, brine, dried, concentrated and purified by prep. silica gel tlc. Titled product was recrystallized from hot ethylate acetate, Mp 128°–129° C. Mass spec. (MS) M$^+$ calculated 452.58; observed 452. Anal.. calcd for $C_{27}H_{36}N_2O_4 \cdot 0.2\ H_2O$, C 71.08; H 8.04; N 6.14; Found C 71.08; H 8.03, N 5.90.

EXAMPLE 4

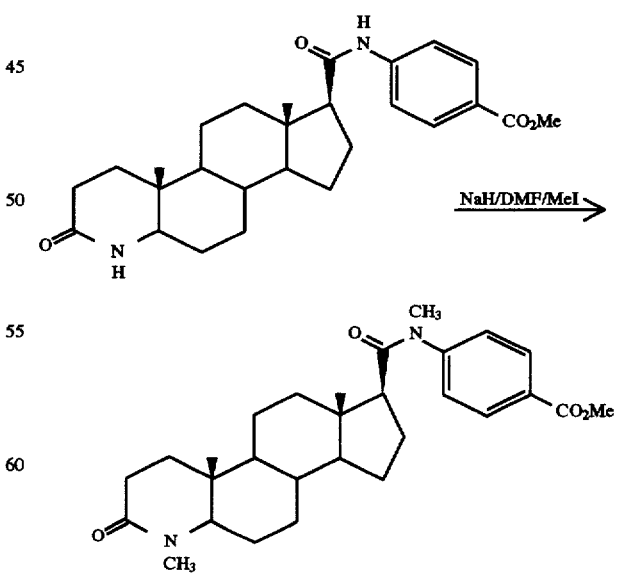

N-methyl-N-4-carbomethoxyphenyl-3-oxo-4-aza-4-methyl-5α-androstane-17β-carboxamide N-4-carboxymethylphenyl-3-oxo-4-aza-5α-androstane-17β-carboxylate (185 mg, 0.41 mmol) was dissolved in 10 ml of DMF and mg of NaH (80% dispersion in mineral oil) was added. After stirring the reaction mixture for 2 hrs at room temperature, 100 micro liter methyl iodide was added. The reaction mixture was stirred further at room temperature for 1 hr, excess of NaH decomposed by careful addition of water, extracted with ethylacetate and organic layer was washed with water, dried and concentrated to give yellow residue. The titled product was purified by column silica gel tlc (30% acetone/$CH_2Cl_2$), Mp 149°–150° C. Mass spec. (MS) $M^+$ calculated 480.63; observed 480. Anal. calcd for $C_{29}H_{40}N_2O_4 \cdot 0.8\ H_2O$, C 72.47; H 8.39; N 5.83; Found C 70.36; H 8.08, N 5.55.

EXAMPLE 5

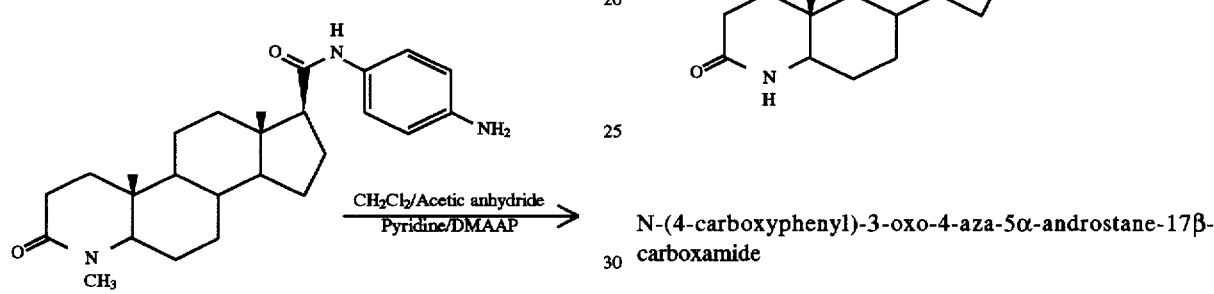

N-(4-isobutyramidophenyl)-3-oxo-4-aza-4-methyl-5α-androstane-17β-carboxamide

To a solution of N-4-aminophenyl-3-oxo-4-aza-4-methyl-5α-androstane-17β-carboxamide (80 mg, 0.195 mmol) in methylene chloride (10 ml) was added DMAP (71.37 mg, 0.585 mmol), pyridine (157 micro liter) and isobutyric anhydride (161.47 micro liter, 0.975 mmol). After stirring the reaction mixture for 40 min. at room temperature, the reaction mixture was diluted with 30 ml of methylene chloride, washed with aq. $NaHCO_3$, aq. HCl, water, brine, dried and concentrated. Residue was purified to yield rifled product by crystallization from ethyl acetate/methylene chloride, Mp 260°–261° C. Mass spec. (MS) $M^+$ calculated 493.70; observed 495 (m+2). Anal. calcd for $C_{30}H_{43}N_3O_3$, C 72.99; H 8.78; N 8.31; Found C 72.96; H 8.70, N 8.34.

EXAMPLE 6

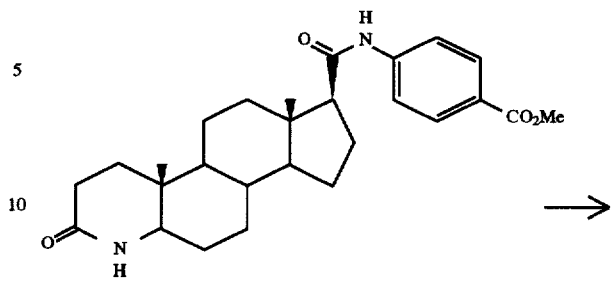

N-(4-carboxyphenyl)-3-oxo-4-aza-5α-androstane-17β-carboxamide

N-4-carboxymethyphenyl-3-oxo-4-aza-5α-androstane-17β-carboxamide (100 mg) was dissolved in methanol (10 ml) and 4 ml of aq. KOH was added. After stirring the reaction mixture for 8 hrs at 50°, the reaction mixture was cooled to room temperature, acidified with aq. HCl and methanol removed under vacuum. The solid obtained was filtered and dried to yield titled product, Mp 355°–357° C.

FLOW SHEET A

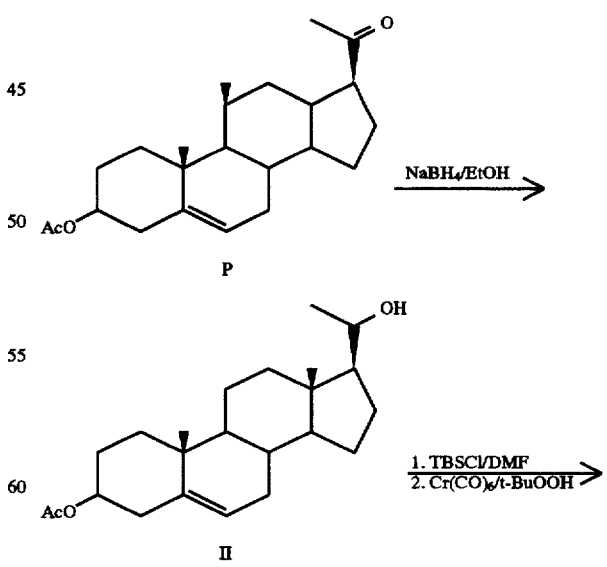

13
-continued
FLOW SHEET A
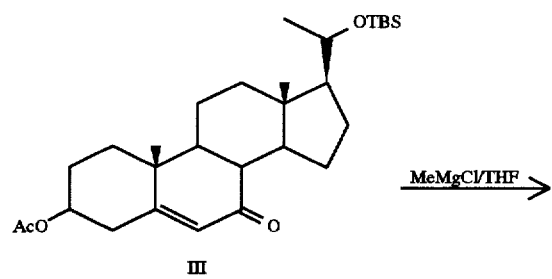
III
MeMgCl/THF →
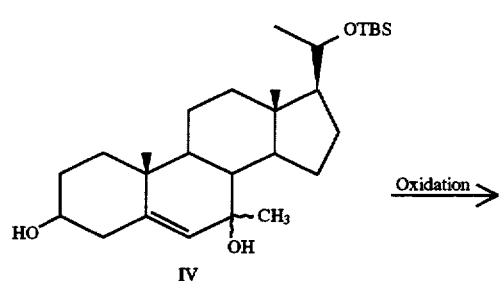
IV
Oxidation →
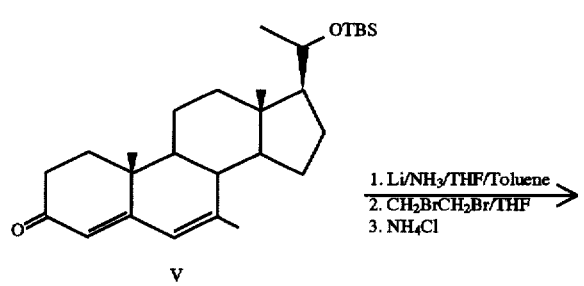
V
1. Li/NH₃/THF/Toluene
2. CH₂BrCH₂Br/THF
3. NH₄Cl
→
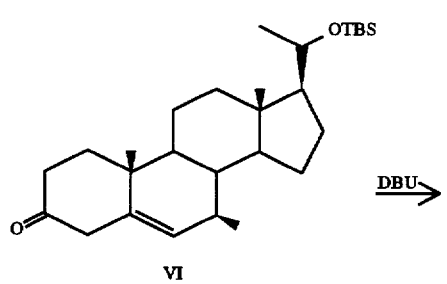
VI
DBU →
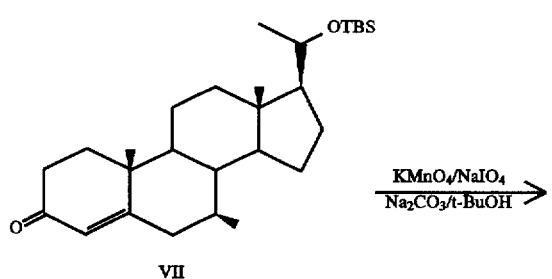
VII
KMnO₄/NaIO₄
Na₂CO₃/t-BuOH →
14
-continued
FLOW SHEET A
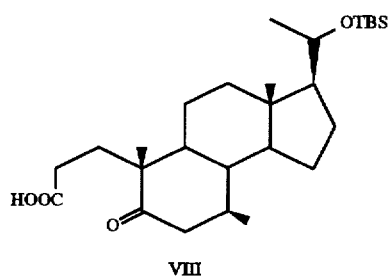
VIII
FLOW SHEET B
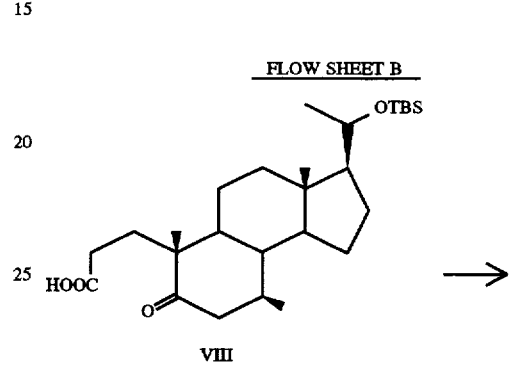
VIII
→
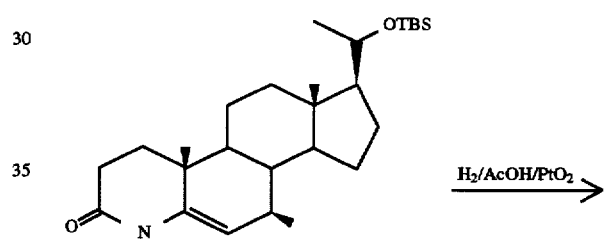
IX
H₂/AcOH/PtO₂ →
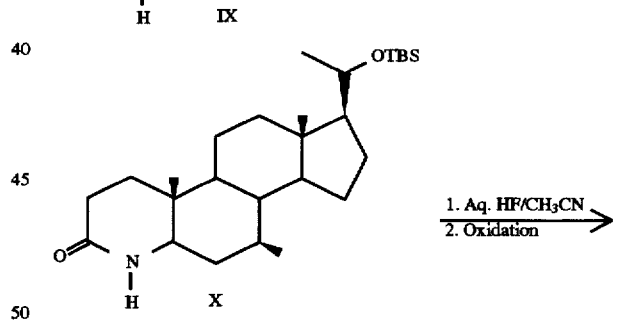
X
1. Aq. HF/CH₃CN
2. Oxidation
→
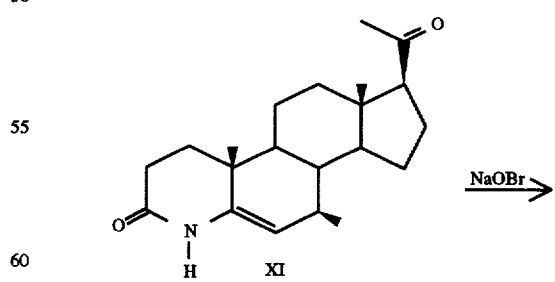
XI
NaOBr →

15
-continued
FLOW SHEET B

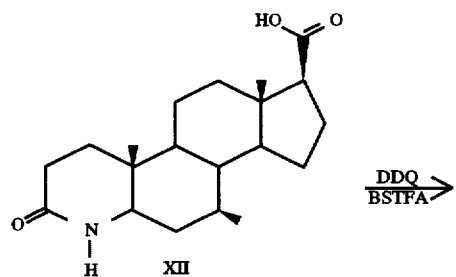

DDQ
BSTFA→

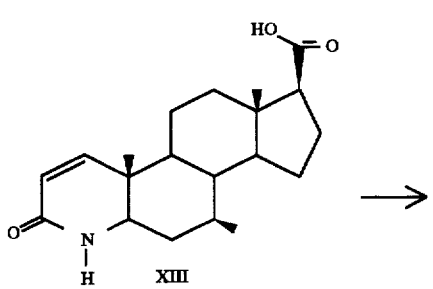

→

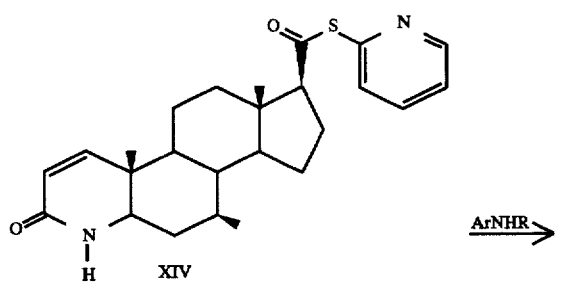

ArNHR→

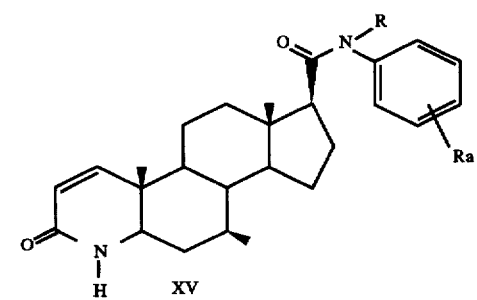

EXAMPLE 7

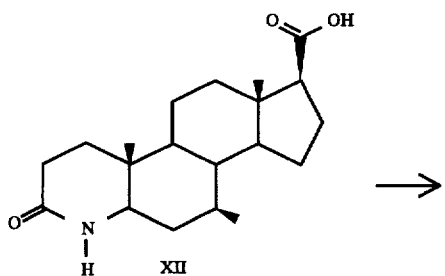

→

16
-continued

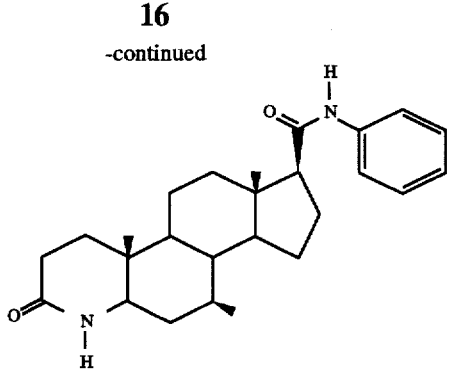

7β-Methyl-3-oxo-4-aza-5α-androstane-17β-(N-phenyl) carboxamide

The intermediate XII is reacted with aldrithiol/PPh₃ analogously as described above to give the corresponding 2-thio-pyridylester.

This in turn is reacted with an excess of aniline at elevated temperature, e.g. 100°–150° C. to yield the above-titled 7β-methyl-azasteroidal anilide.

Similarly, using other substituted anilines, other azasteroidal anilides can be produced as described herein.

Preparation of the Starting Material XII

As seen in the Flowsheets A and B, pregnenolone-3-acetate P is first reduced to the alcohol II by sodium borohydride in ethanol at –10° to 0° C. The alcohol II is then protected by a dimethyl-t-butyl silyl (TBS) group in DMF with TBS chloride and imidazole as a base at room temperature. The protected alcohol is then oxidized to the corresponding 5-en-7-one III by treatment with hydrogen t-butyl peroxide and chromium hexacarbonyl in e.g., acetonitrile, at reflux. The 7-methyl group can be introduced at this point by a Grignard reaction using e.g., methyl magnesium chloride in e.g., anhydrous THF at 0° to –10° C. to produce the 7-methyl-7-hydroxy adduct IV. This is then oxidized with e.g. aluminum isopropoxide and cyclohexanone (Oppenauer oxidation conditions) in refluxing toluene solvent to produce the 7-methyl-4,6-dien-3-one V. This in turn is reduced via e.g., metal-ammonia, THF and toluene at –78° C. to selectively yield the 7-beta-methyl-5-en-3-one VI. In the next step the delta-5 double bond is isomerized to the 4-ene by use of DBU (1,8-diazabicyclo[5.4.0] undec-7-ene) in e.g. refluxing tetrahydrofuran (THF) to produce the 7-methyl-4-ene-3-one, VII. The A ring is next cleaved by treatment with e.g. potassium permanganate, sodium periodate in t-butyl alcohol at 80° C. to produce the corresponding seco-acid VIII.

Treatment of the seco-acid with ammonium acetate in glacial acetic acid at 120° C. yields e.g., the 7-methyl-4-aza-pregn-5-en-3-one IX. This in turn is selectively reduced with e.g., PtO₂, to remove the 5-double bond to produce the 5α-hydrogen compound X. The TBS protecting group is next removed by aqueous HF in acetonitrile at room temperature and then oxidized by tetrapropylammonium perruthenate/4-methylmorpholine N-oxide in methylene chloride at room temperature to yield the 17-acetyl compound XI. This is treated with a sodium hypobromite/sodium hydroxide solution in dioxane at 10°–15° C. to form the starting intermediate 17-carboxylic acid XII, mp. 311°–312+ C. This is then used as described above to make the 2-thiopyridyl ester and the resulting azasteroidal anilides.

The 1,2-double bond in the A ting can be introduced into XII by DDQ oxidation (see procedure in U.S. Pat. No. 5,084,574) to produce XIII, mp. 328°–330° C. Formation of the 2-thiopyridyl intermediate XIV, analogously as described above, and reaction with aniline or substituted anilines as described above produces the corresponding anilides, XV where Ra represents X, Y, Z substituents on the aniline ring.

What is claimed is:

1. A compound of the formula:

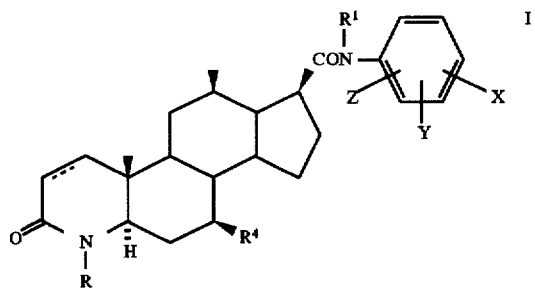

wherein:

R is H, $CH_3$, or $C_2H_5$;

$R^1$ is H, $C_1$–$C_{10}$ alkyl, or phenyl; and

X, Y and Z independently represent —H; SH; —S$C_1$-$C_4$alkyl; —$C_2$-$C_{10}$ acyl; aryl; —CONR$^2$R$^3$ where R$^2$ and R$^3$ independently are H, $C_{1-8}$ alkyl, $C_{3-8}$ cycloalkyl, or aryl;

—NHCOR$^2$;
—OCOR$^2$;
—NR$^2$(CO)R$^3$;
—NR$^2$(CO)NHR$^3$;
—NHSO$_2$R$^2$;
—OR$^2$;
—NR$^2$R$^3$;
—CO$_2$R$^2$;

provided that X, Y, and Z cannot simultaneously be —H when $R^1$ is —H or $C_{1-10}$ alkyl, and provided further that X, Y, and Z cannot simultaneously be —H when $R^1$ is phenyl and $R^4$ is —H or methyl;

$R^4$ is selected from:

alpha-hydrogen and beta-hydrogen or beta-$C_1$-$C_4$ alkyl; wherein aryl is phenyl;

and wherein the dashed line can represent a double bond when present;

and wherein at least two of X, Y and Z are hydrogen; and pharmaceutically acceptable salts thereof.

2. The compound selected from the group consisting of:

N-(4-hydroxyphenyl)-3-oxo-4-aza-5α-androst-1-ene-17β-carboxamide,

N-(3-hydroxyphenyl)-3-oxo-4-aza-5α-androst-1-ene-17β-carboxamide,

N-(2-hydroxyphenyl)-3-oxo-4-aza-5α-androst-1-ene-17β-carboxamide, phenyl-3-oxo-4-aza-5α-androst-1-ene-17β-carboxamide, N-(4-aminophenyl)-3-oxo-4-aza-5α-androst-1-ene-17β-carboxamide, N-(3-aminophenyl)-3-oxo-4-aza-5α-androst-1-ene-17β-carboxamide, N-(2-aminophenyl)-3-oxo-4-aza-5α-androst-1-ene-17β-carboxamide, N-(4-carbomethoxy)phenyl-3-oxo-4-aza-5α-androstane-17β-carboxamide, N-(4-carbomethoxy)phenyl-3-oxo-4-aza-5α-androst-1-ene-17β-carboxamide, N-(4-carboxyphenyl)-3-oxo-4-aza-5α-androstane-17β-carboxamide, N-(4-carbomethoxy)phenyl-N-methyl-3-oxo-4-methyl-4-aza-5α-androstane-17β-carboxamide, N-(4-carbomethoxy)phenyl-N-methyl-3-oxo-4-methyl-4-aza-5α-androst-1-ene-17β-carboxamide, N-(2-carbomethoxy)phenyl-3-oxo-4-aza-5α-androstane-17β-carboxamide, N-(2-carbomethoxy)phenyl-3-oxo-4-aza-5α-androst-1-ene-17β-carboxamide, N-(4-aminophenyl)-3-oxo-4-aza-5α-androstane-17β-carboxamide, N-(4-aminophenyl)-3-oxo-4-methyl-4-aza-5α-androstane-17β-carboxamide, N-4-acetamidophenyl-N-acetyl-3-oxo-4-methyl-4-aza-5α-androstane-17β-carboxamide, N-(4-acetamido)phenyl-3-oxo-4-methyl-4-aza-5α-androstane-17β-carboxamide, N-(4-acetamidophenyl-3-oxo-4-aza-5α-androstane-17β-carboxamide, N-(4-pivalamido)phenyl-3-oxo-4-methyl-4-aza-5α-androstane-17β-carboxamide, and N-(4-isobutyramido)phenyl-3-oxo-4-methyl-4-aza-5α-androstane-17β-carboxamide.

3. The compound selected from

N-4-aminophenyl-3-oxo-4-aza-5α-androst-1-ene-17β-carboxamide, and

N-(4-isobutyramidophenyl)-3-oxo-4-aza-4-methyl-5α-androstane-17β-carboxamide.

* * * * *